(12) United States Patent
White et al.

(10) Patent No.: US 7,644,898 B2
(45) Date of Patent: Jan. 12, 2010

(54) MEDICAL BOOM WITH ARTICULATED ARMS AND A BASE WITH PRECONFIGURED REMOVABLE MODULAR RACKS USED FOR STORING ELECTRONIC AND UTILITY EQUIPMENT

(75) Inventors: Paul White, Lake Oswego, OR (US); Larry Vollum, Portland, OR (US); Dennis Palatov, Portland, OR (US)

(73) Assignee: CompView Medical, LLC, Beaverton, OR (US)

( * ) Notice: Subject to any disclaimer, the term of this patent is extended or adjusted under 35 U.S.C. 154(b) by 265 days.

(21) Appl. No.: 11/686,090

(22) Filed: Mar. 14, 2007

(65) Prior Publication Data

US 2007/0176060 A1    Aug. 2, 2007

Related U.S. Application Data

(63) Continuation-in-part of application No. 11/093,075, filed on Mar. 28, 2005, now Pat. No. 7,516,924.

(60) Provisional application No. 60/785,052, filed on Mar. 22, 2006.

(51) Int. Cl.
*F16M 11/00* (2006.01)
(52) U.S. Cl. .................... 248/176.1; 248/158; 248/917; 248/919; 248/921; 211/26
(58) Field of Classification Search ......... 248/917–923, 248/158, 176.1, 276.1; 211/26; 361/800
See application file for complete search history.

(56) References Cited

U.S. PATENT DOCUMENTS 4,548,373 A    10/1985    Komura
(Continued)

FOREIGN PATENT DOCUMENTS

DE    9218373.5    12/1992
(Continued)

OTHER PUBLICATIONS

International Search Report dated Jun. 19, 2008 from International Application No. PCT/US06/3708.
(Continued)

*Primary Examiner*—Amy J. Sterling
(74) *Attorney, Agent, or Firm*—Beyer Law Group LLP

(57) ABSTRACT

The present invention is directed to a medical boom with articulated arms and a base cabinet designed to accommodate modular equipment and utility racks that include video processing, computer, and electronic, and other utility equipment that can be easy inserted and removed from the base cabinet is disclosed. The boom includes a stationary base that is configured to be installed into an operating room and one or more boom arms supported by the stationary base and configured to extend over an operating table in the operating room. The structural base includes one or more bays configured to receive a modular rack of electrical equipment. In various embodiments, the structural base cabinet further incorporates wiring to connect the equipment installed in the modular racks to video monitors and other equipment mounted on the articulated booms. The modular racks are preconfigured with a variety of electronic equipment such as computers, video processors and the like. The modular racks are installed in the base cabinet subsequent to the cabinet's structural installation in the operating room and may be readily removed or replaced at a later time.

19 Claims, 11 Drawing Sheets

U.S. PATENT DOCUMENTS

| | | | |
|---|---|---|---|
| 5,618,090 A * | 4/1997 | Montague et al. | 312/209 |
| 5,878,536 A * | 3/1999 | Demmitt et al. | 52/36.4 |
| 6,012,821 A | 1/2000 | Yeaney et al. | |
| 6,202,360 B1 | 3/2001 | Rattner et al. | |
| 6,328,458 B1 | 12/2001 | Bell et al. | |
| 6,639,789 B2 | 10/2003 | Beger | |
| 6,725,483 B2 * | 4/2004 | Gallant et al. | 5/658 |
| 6,732,988 B2 | 5/2004 | Ihalainen et al. | |
| 6,793,625 B2 | 9/2004 | Cavallaro et al. | |
| 6,817,585 B2 | 11/2004 | Wagner et al. | |
| 6,840,486 B2 | 1/2005 | Kuhn | |
| 6,857,609 B2 | 2/2005 | Stoianovici et al. | |
| 6,896,233 B2 | 5/2005 | Kuhn | |
| 7,156,475 B2 * | 1/2007 | Gloger, Jr. | 312/216 |
| 7,246,780 B2 | 7/2007 | Oddsen, Jr. | |
| 7,254,850 B2 * | 8/2007 | Newkirk et al. | 5/600 |
| 2002/0179549 A1 * | 12/2002 | Felcman et al. | 211/26 |
| 2004/0073279 A1 * | 4/2004 | Malackowski et al. | 607/88 |
| 2004/0188578 A1 | 9/2004 | Turner | |
| 2006/0065795 A1 * | 3/2006 | Blackburn | 248/122.1 |
| 2007/0102607 A1 * | 5/2007 | Koh | 248/276.1 |

FOREIGN PATENT DOCUMENTS

| | | |
|---|---|---|
| DE | 19807241 | 2/1998 |
| DE | 19807242 | 2/1998 |
| DE | 19807243 | 2/1998 |
| EP | 0876799 | 11/1998 |
| WO | WO99/23989 | 5/1999 |
| WO | WO 02/30348 | 4/2002 |

OTHER PUBLICATIONS

Written Opinion dated Jun. 19, 2008 from International Application No. PCT/US06/3708.

Esco Medicon Price List from the Mar. 2005 Catalog, http://www.escoindustries.com/au/html/pg93-99.html, downloaded Mar. 26, 2005, pp. 93-99.

* cited by examiner

MEDICAL BOOM WITH ARTICULATED ARMS AND A BASE WITH PRECONFIGURED REMOVABLE MODULAR RACKS USED FOR STORING ELECTRONIC AND UTILITY EQUIPMENT

RELATED APPLICATIONS

This application claims priority of U.S. Provisional Patent Application No. 60/785,052, filed Mar. 22, 2006, entitled "MODULAR INTEGRATED VIDEO PRESENTATION" which is hereby incorporated by reference. The subject application is also a Continuation-in-Part of U.S. application Ser. No. 11/093,075, filed Mar. 28, 2005 now U.S. Pat. No. 7,516,924, entitled "ARTICULATED BOOM FOR SUPPORTING VIDEO AND MEDICAL EQUIPMENT IN HOSPITAL OPERATING ROOMS," incorporated herein for all purposes, and assigned to the same assignee of the present application.

FIELD OF THE INVENTION

The present invention relates to a medical boom with one or more articulated arms used to suspend video displays for use in a hospital operating room, and more particularly, to a medical boom having a base cabinet designed to accommodate modular equipment racks and utility cabinets which enable the easy insertion and removal of video processing, computer, electronic and other equipment into or out of the base cabinet.

BACKGROUND

State of the art hospital operating rooms now contain a wide variety of audio, visual and technology tools, such as video cameras, video recorders, microphones and voice recorders, video guided ultrasound imaging systems, lasers, cytoscanners, etc. With delicate surgery for example, a video camera may be placed in or above the surgical area of the patient. The image from the camera is then transmitted to a large display, such as a flat panel, allowing the operating doctor and medical staff to see an enlarged visual of the surgical area. The enlarged image makes it easier for the doctor to perform the surgery compared to relying on the naked eye.

U.S. application Ser. No. 11/093,075, entitled "ARTICULATED BOOM FOR SUPPORTING VIDEO AND MEDICAL EQUIPMENT IN HOSPITAL OPERATING ROOMS", incorporated herein for all purposes, and assigned to the same assignee of the present application, describes a medical boom used for suspending video and other equipment in a hospital operating room. The medical boom disclosed in the above-mentioned application features articulated arms attached to a structural equipment cabinet that is mounted to the floor or wall of the operating room. Electronic equipment is installed or mounted directly in the cabinet at the factory prior to shipment to customer facility such as a hospital operating room. While the aforementioned medical boom does dramatically lower installation time and cost compared to previously known approaches in the prior art, the requirement of installing electronic equipment in the structural cabinet of the medical boom in the factory, as opposed to on site, is less than ideal. Due to size and weight of the cabinet, the medical boom is typically transported by truck. The cabinet and pre-installed equipment are therefore subject to vibration, shock and adverse temperatures and humidity conditions during transit, all of which could potentially damage the electronic equipment. Alternatively, if the electronic equipment is shipped separately, it has to be installed and configured on site, requiring a team of technicians to travel to the customer facility, adding to the time and expense of the installation.

A medical boom with articulated arms and a base cabinet designed to accommodate modular equipment and utility racks that include video processing, computer, and electronic, and other utility equipment that can be easy inserted and removed from the base cabinet is therefore needed.

SUMMARY OF THE INVENTION

A medical boom with articulated arms and a base cabinet designed to accommodate modular equipment and utility racks that include video processing, computer, and electronic, and other utility equipment that can be easy inserted and removed from the base cabinet is disclosed. The boom includes a stationary base that is configured to be installed into an operating room and one or more boom arms supported by the stationary base and configured to extend over an operating table in the operating room. The structural base includes one or more bays configured to receive a modular rack of electrical equipment. In various embodiments, the structural base cabinet further incorporates wiring to connect the equipment installed in the modular racks to video monitors and other equipment mounted on the articulated booms. The modular racks are preconfigured with a variety of electronic equipment such as computers, video processors and the like. The modular racks are installed in the base cabinet subsequent to the cabinet's structural installation in the operating room and may be readily removed or replaced at a later time. The placement of equipment into preconfigured modular racks allows such equipment to be transported and handled separately from the structural base cabinet while allowing it to be preconfigured as a system. This prevents damage to sensitive equipment during transport, enables faster installation, and facilitates rapid maintenance and upgrades of the equipment after it is placed in service.

BRIEF DESCRIPTION OF THE DRAWINGS

The invention, together with further advantages thereof, may best be understood by reference to the following description taken in conjunction with the accompanying drawings in which.

It should be noted that like reference numbers refer to like elements in the figures.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

Figure 1:
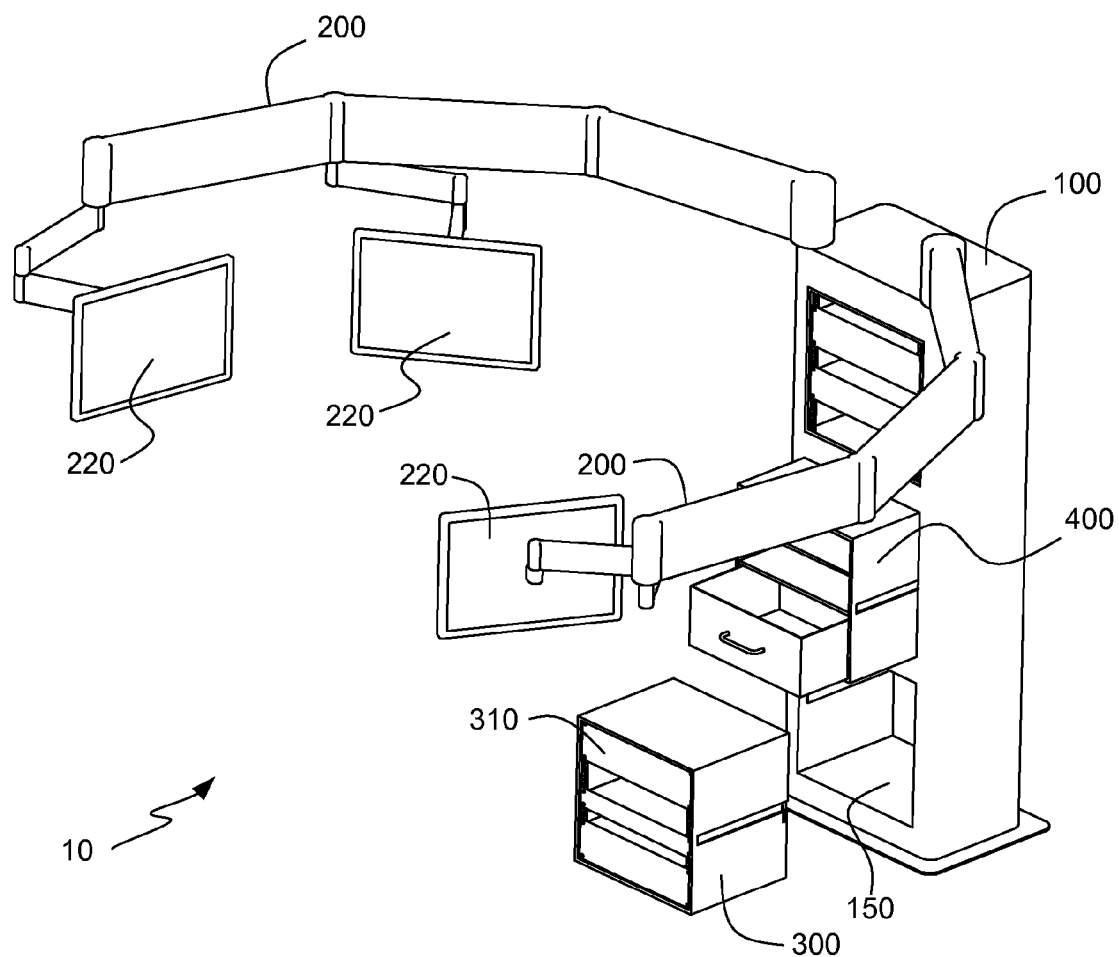
FIG. 1 illustrates medical boom with articulated arms and a base cabinet designed to accommodate modular equipment racks according to the present invention.

Referring to FIG. 1, a medical boom with articulated arms and a base cabinet designed to accommodate modular equipment racks according to the present invention is shown. The medical boom 10 includes a base cabinet 100, one or more articulated arms 200, and a plurality of video displays 220 suspended from the articulated arms 200. The base cabinet 100 includes a number of equipment bays 150. The equipment bays 150 are used for accommodating either equipment racks 300 and/or utility modules 400. For more details on the design of the base cabinet 100 and articulated arms 200 of the medical boom 10, see the aforementioned pending U.S. application Ser. No. 11/093,075, incorporated by reference herein for all purposes.

Figure 2A:
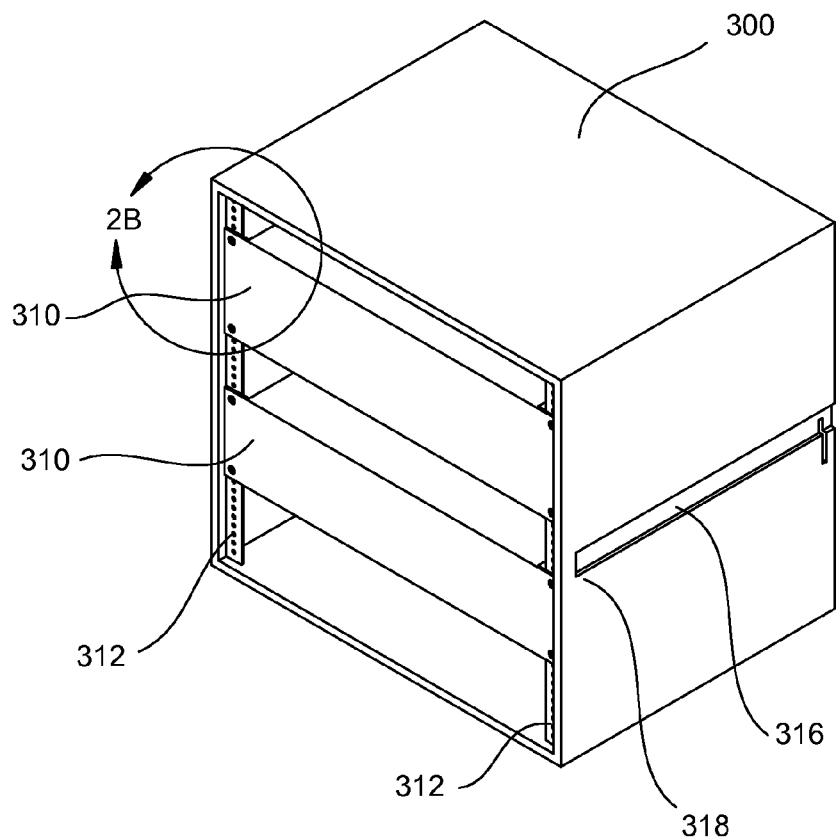
FIGS. 2A and 2B illustrate a modular equipment rack for use with the base cabinet of the medical boom of the present invention.
Figure 2B:
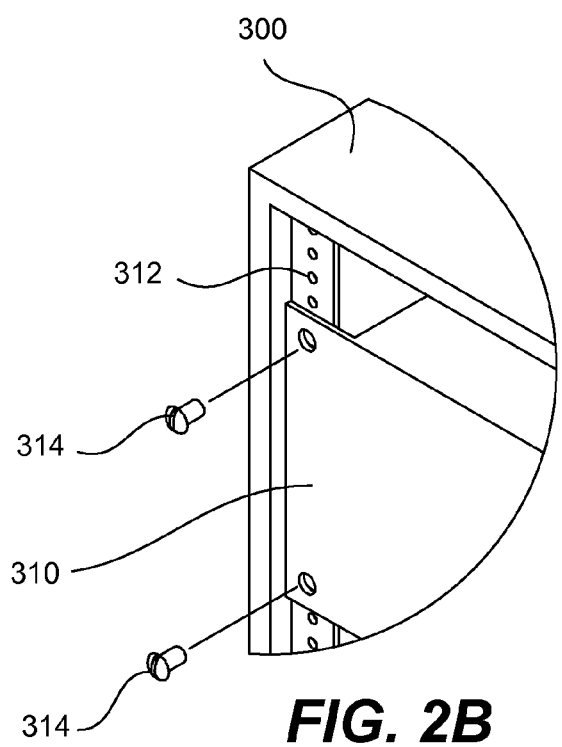

Referring to FIGS. 2A and 2B, a modular equipment rack 300 for use with the base cabinet 100 of the medical boom 10 according to one embodiment is shown. The equipment rack 300 is a rectangular shaped box or cabinet configured to house electronic equipment 310. The front face of the rack 300 includes a pair mounting brackets 312, each with a plurality of threaded holes. As illustrated in FIG. 2B, screws are used to screw or mount the equipment 310 into the mounting brackets 312 of rack 300. As illustrated in the two figures, one or more pieces of electronic equipment 310 can be housed in the rack 300. The equipment rack 300 also includes a pair of guides 316 and stops 318 located on opposite sides of the cabinet (in the FIG. 2A, only one groove 316 and stop 318 is visible). The guides 316 are used to install the rack 300 into the equipment bays 150 of the base cabinet 100, as described in more detail below.

Figure 3:
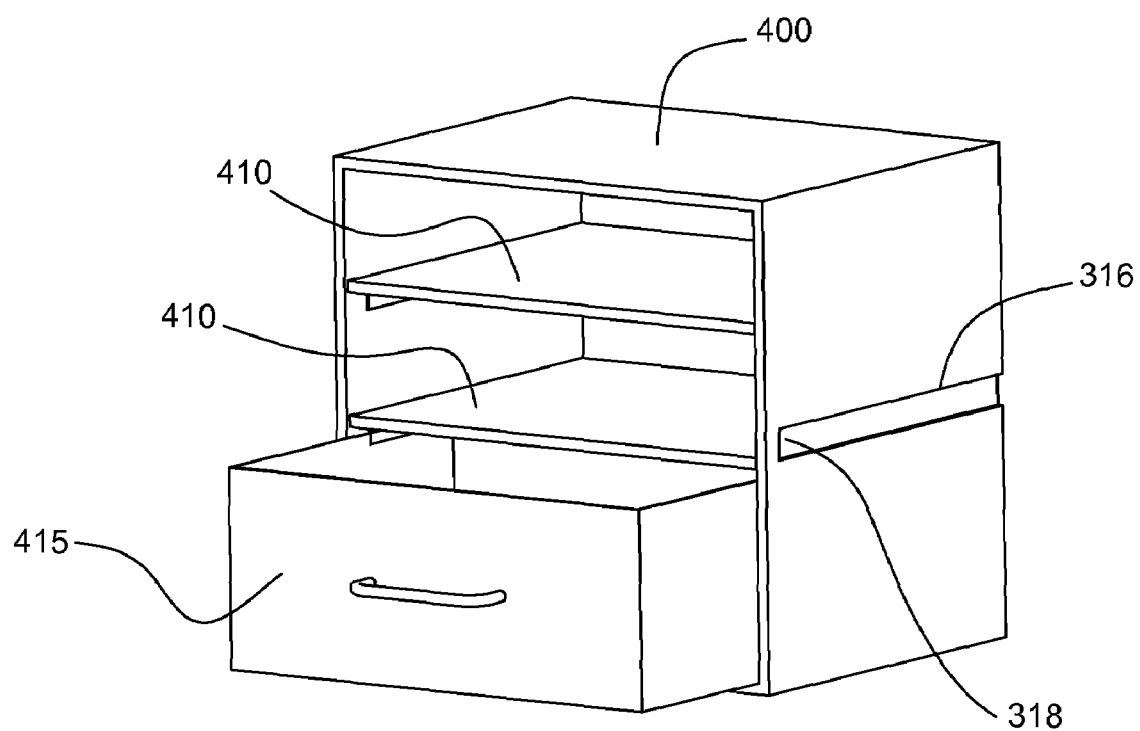
FIG. 3 illustrates a utility module that may be installed in the base cabinet of the medical boom in lieu of a modular equipment rack according to the present invention.

Referring to FIG. 3, a utility module 400 that may be installed in the base cabinet 10 of the medical boom 10 in lieu of a modular equipment rack 300 according to the present invention is shown. The utility module 400 is also a rectangular shaped box or cabinet configured to store utility medical equipment, such as surgical tools and the like. The utility module 400 includes one or more shelves 410 and one or more draws 415. The utility module also includes a pair of guides 316 and stops 318 also located on opposite sides of the cabinet (only one guide 316 and stop 318 are visible in the figure). The guide rails 316 are used to install the utility module 400 into the equipment bays 150 of the base cabinet 100, as described in more detail below. It should be noted that utility module 400 does not necessarily require a combination of shelves 410 and draws 415. In alternative embodiments, the modules 400 may include just one or more shelves 410 or just one or more draws 415.

In accordance with one embodiment, the equipment racks 300 and the utility modules 400 are the same size and are inter-changeable. Each can be inserted into any one of the equipment bays 150 of the base cabinet 100 to configure the medical boom 10 in any manner desired. It should be noted, however, that the racks 300 and modules 400 do not necessarily have to be the same size. The bays 150 in the base cabinet 100 can e made of any size and the racks and/or modules 400 can be made the appropriate size to fit into the bays 150.

Figure 4A:
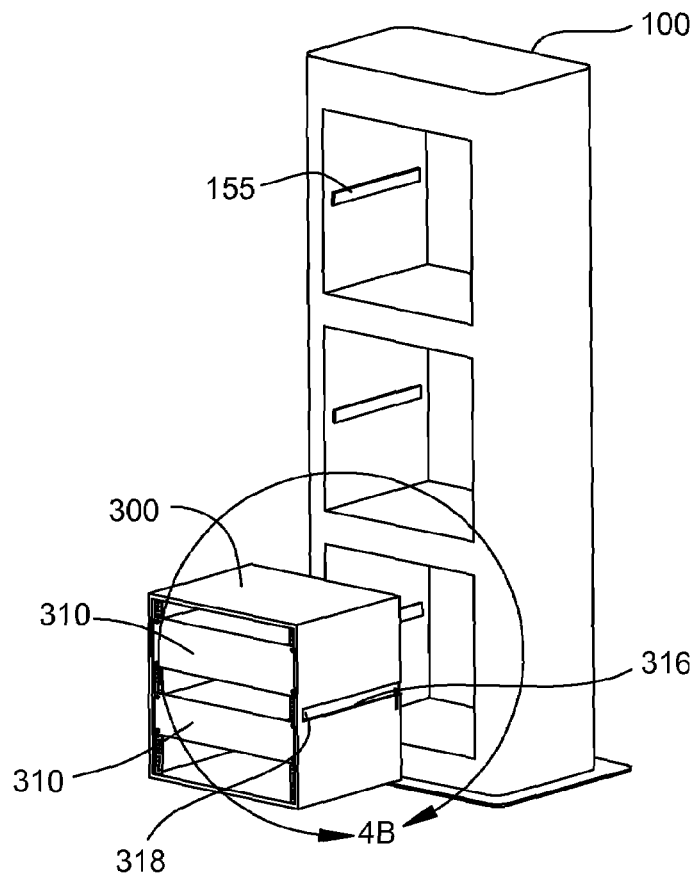
FIGS. 4A-4B illustrate two drawings showing the installation of a modular electronic equipment rack in the base cabinet of the present invention.
Figure 4B:
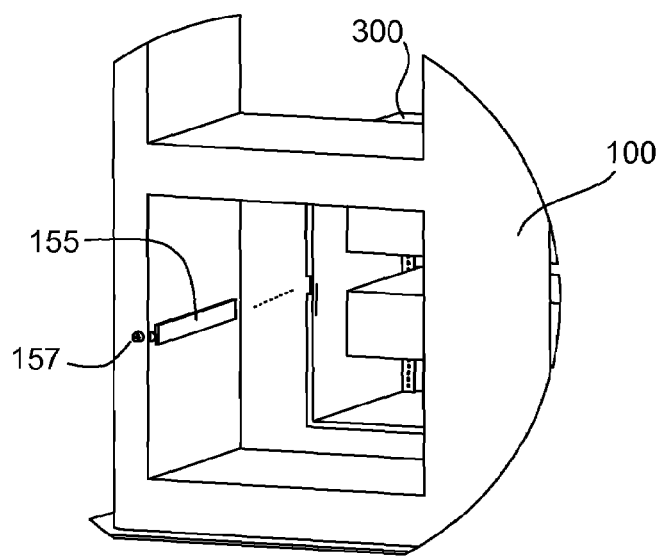

Referring to FIGS. 4A and 4B, the installation of a modular equipment rack 300 in the base cabinet 100 of the present invention is illustrated. In FIG. 4A, an equipment rack 300 is shown being positioned for installation into a bay 150 of the base cabinet 100. In FIG. 4B, a pair of guide rails 155, provided within each bay 150, are shown (only one guide rail 155 is visible). The two guides 316 on the opposite sides of either the rack 300 and/or utility module 400 are configured to engage and move along the two guide rails 155 provided in each bay 150. The stops 318, located at the end of each of the guides 316, prevent the rack 300 or utility module 400 from sliding through the back of the base cabinet 100. A lock 157 is provided within the structure of the base cabinet 100 to lock either the rack 300 or utility module 400 in place once installed in the bay 150.

Figure 5:
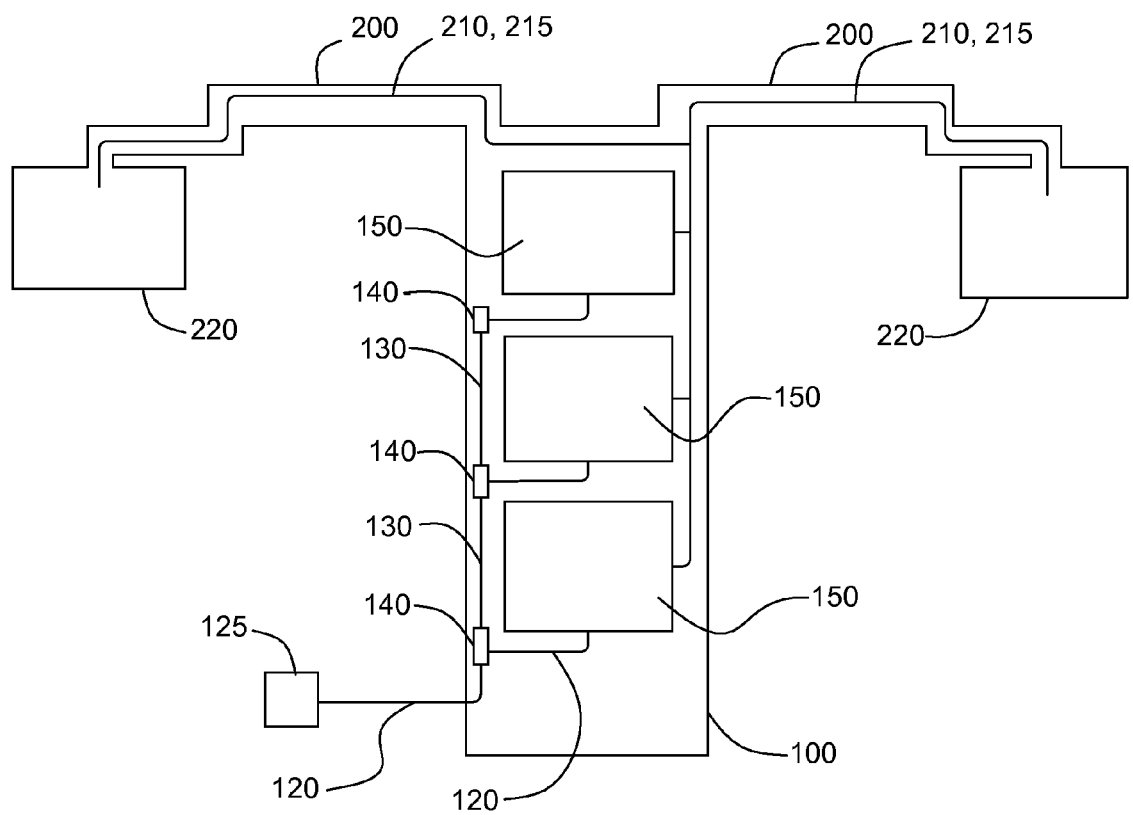
FIG. 5 is a cross section diagram illustrating an exemplary routing for the electrical cabling used for the video display and electronics housed in the medical boom of the present invention.

FIG. 5 is a cross section diagram illustrating an exemplary routing for the electrical cabling used for the video display and electronics housed in the medical boom 10 of the present invention. The cross section shows the routing of video 210 and power cabling 215 between the video displays 220 suspended by the articulated arms 200 connected to the bays 150 in the base cabinet 10. The cross section also shows electrical wiring 120, conduit 130, and junction boxes 140 between a power supply 125 and the bays 150. The aforementioned electrical wiring 120, conduit 130, and junction boxes 140 are pre-installed in the base cabinet 100 prior to shipment to a customer facility. During installation of the racks 300 and/or modules 400 at the customer facility (an operating room or other medical facility), the video 210 and power cabling 215 are connected along with electrical wiring 120 and conduit wiring 130 to the equipment in the bays 150.

The medical boom 10 of the present invention thus provides a flexible, self-contained medical video presentation unit that can be quickly and easily installed in an existing operating room. With the bays 150 in the base cabinet, electrical equipment in the equipment racks 300 and other utilities in the utility modules 400 can readily be installed on site in the hospital operating room. In the event the electronic equipment needs to be service or repaired, the racks 300 can be readily be removed and the equipment repaired or replaced, with minimum down time.

In the one embodiment, a structural cabinet 100 is shipped to the customer facility along with articulated boom arms 200. One or more equipment racks 300 and/or utility modules 400 are then configured with electronic equipment 310 and other utility equipment according to customer requirements at a location remote from the customer. After configuration and testing, the racks 300 of equipment 310 and/or modules 400 are then separately shipped to the customer facility, either simultaneously or at a different time as the cabinet 100. The required video monitors 220 are can be either shipped together with either the racks 300, the boom 10, or separately.

At the customer facility, the base cabinet 100 is first structurally attached to the facility floor in the desired location. The base cabinet is affixed to the floor or wall of the operating room using any one of a number of known elements such as concrete anchors, bolts, studs, structural adhesives or a combination thereof. Upon completion of the structural installation, the installation of the necessary electrical power or signal cabling is carried out to connect the electrical wiring and conduit in the base cabinet 100. Next, the articulated boom arms 200 are mounted to the base cabinet 100 and the video monitors 220 are attached to the booms 200. To complete the installation of the present invention, one or more of the preconfigured equipment racks 300 are installed into the equipment bays 150 of the base cabinet 100. One or more of the equipment bays 150 may also receive a utility module 400. As a final step, electrical connections are made to the installed electrical equipment 310 and then the entire system is powered up and tested.

In an alternative embodiment, one or more equipment bays may be configured with protective covers or user-accessible doors to protect the electronic equipment contained therein and to optionally limit user access thereto.

Should service or configuration changes be required after the system of the present invention is placed in service, one or more of the equipment racks 300 can be readily removed, serviced, or replaced with another preconfigured equipment rack. The complete racks 300 can be easily shipped to the factory for service or configuration. A replacement preconfigured rack 300 can be shipped to the customer facility in advance and quickly exchanged in the field with any troubleshooting and configuration being performed offline, resulting in the minimum possible downtime and cost.

Figure 6A:
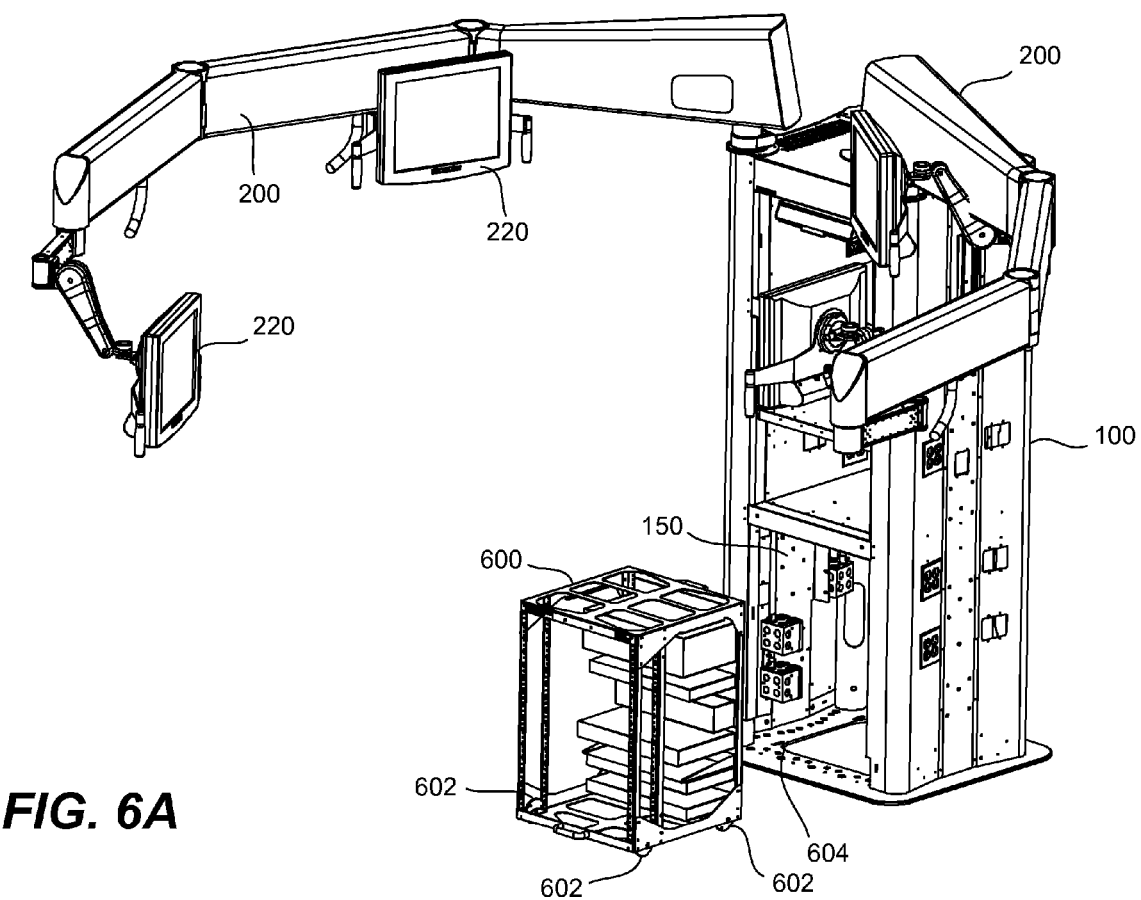
FIGS. 6A-6C illustrate an alternative embodiment of the modular equipment rack in accordance with another embodiment of the invention.
Figures 6B, 6C:
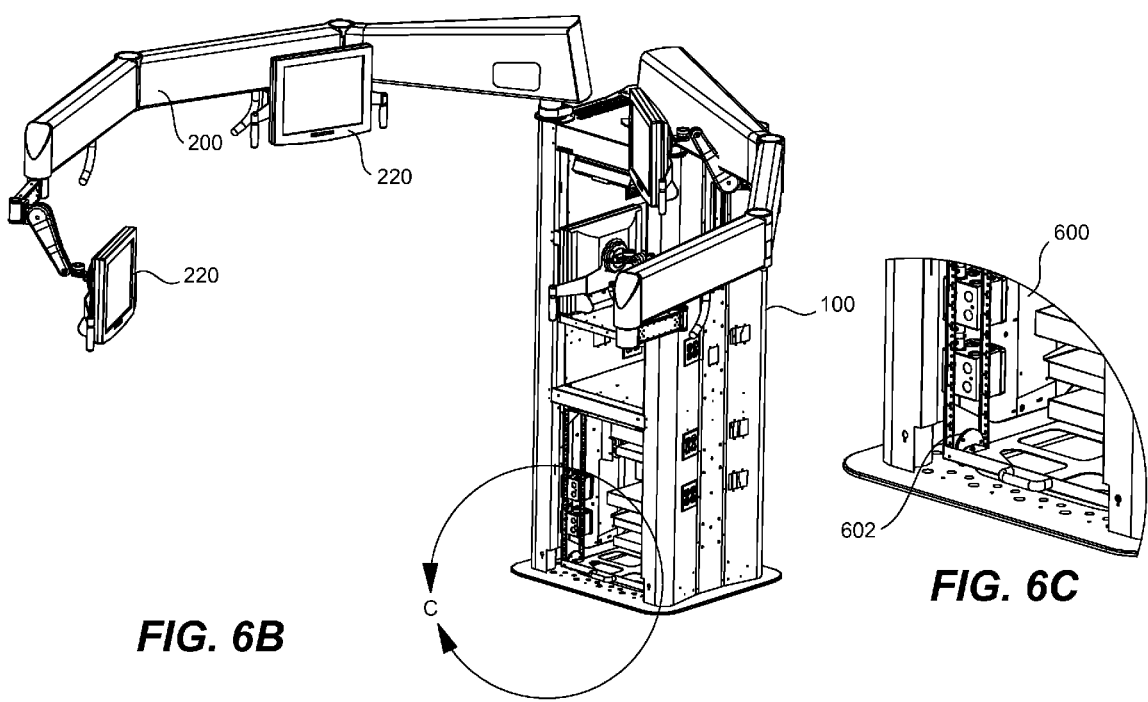

Referring to FIGS. 6A-6C, an alternative embodiment of the modular equipment rack is shown. In this embodiment, the equipment rack 600 includes a plurality of trolley wheels 602, each located at the bottom four corners of the rack 600. The trolley wheels 602 are designed to allow the equipment rack 600 to be readily rolled around. The trolley wheels 602 also facilitate in the installation of the rack 600 into the bays 150 of the base cabinet 100 of the boom 10. A plurality of slots 604 are provided in the bay 150 in the bottom of the base cabinet 100, as best illustrated in FIG. 6A. Although not clearly illustrated in the figure, the slots 604 are provided to accommodate the trolley wheels 602 of the rack 600. During installation, the rack 600 is rolled into the equipment bay 150 until the trolley wheel 602 drop into the slots 604 of the cabinet 100. With the trolley wheels 602 in the slots 604, the rack 600 is "locked" into place within the boom 10. To remove the rack 600, a firm pull on the rack is required to pull the trolley wheels 602 out of the slots 604. The rack 600 can thereafter be rolled out of the equipment bay and readily accessed for repairs or upgrades. FIGS. 6B shows the rack 600 inside the bay 150. FIG. 6C shows an exploded view of one of the wheels 602 of the rack 600 dropped into place within a slot 604 of the base cabinet 100.

Figure 7:
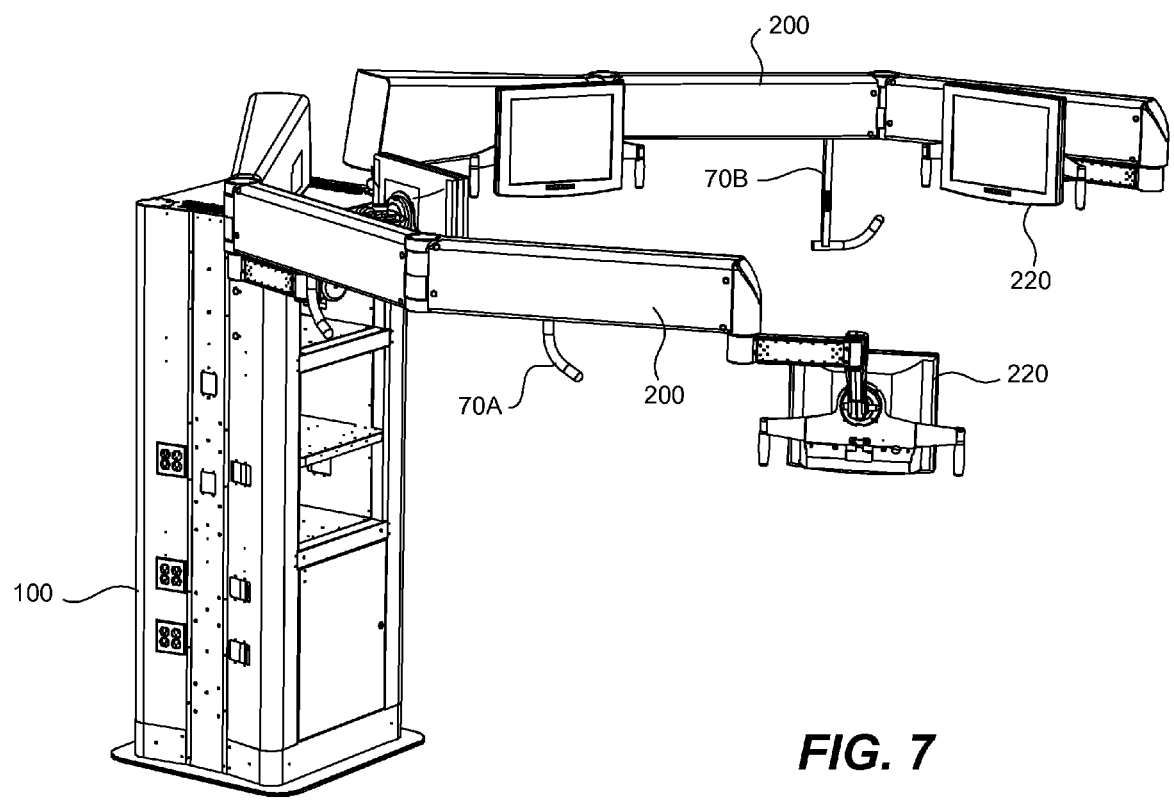
FIG. 7 illustrates retractable arms on the articulated arms of the medical boom in accordance with another embodiment of the invention.

Referring to FIG. 7, the articulated arms 200 with retractable handles 70 are shown in accordance with another embodiment of the invention. One or more handles 70 are provided on each articulated arm 200 for the purpose of facilitating the movement of the video displays 220 and other supported equipment into position. For the sake of illustration, a first handle 70A is shown in a retracted position, while handle 70B is shown in the non-retracted position. When the handle 70 is not in use, it may be partially housed within the articulated arm 220. When the arm 200 is to be positioned, the exposed portion of the handle is pulled down into the non-retracted position. The handle 70 is then used to move the articulated arm 200 so the display monitors 220 are positioned to a desired location. The handle 70 provides a higher degree of leverage, making it easier to move the articulated arms 200 into a desired position. It also makes it easier for members of the medical staff in the operating room who are not very tall to be able to move or manipulate the position of the arms 200 and display monitors 220.

Figure 8A:
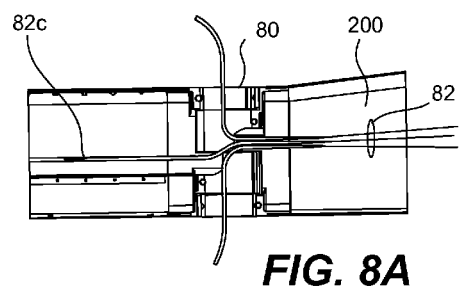
FIGS. 8A-8B illustrate the routing of power and signal wires through the segments and joints of the articulated arm of the medical boom in accordance with the present invention.
Figure 8B:
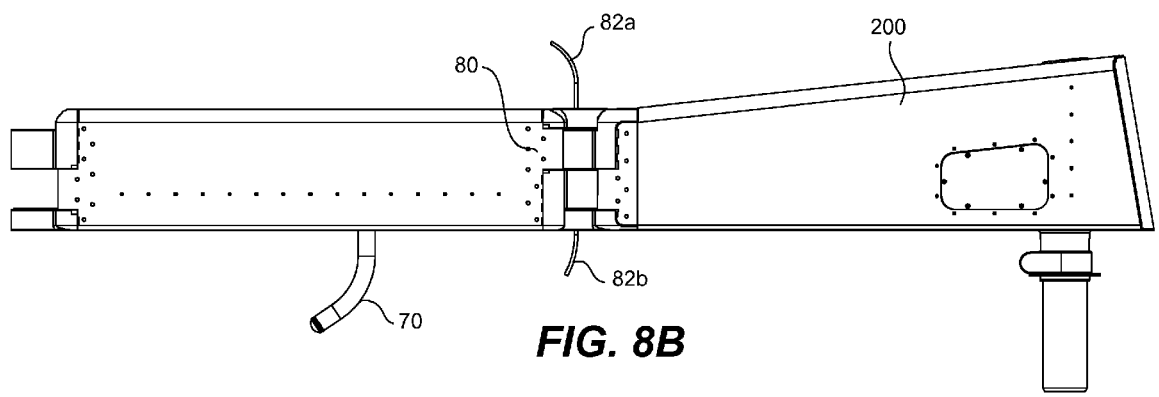

FIGS. 8A-8B illustrate yet another feature of the articulated arms 200 of the present invention. With this embodiment, the articulated arms 200 include a plurality segments joined together by joints 80. The segments include recesses that allow for the routing of wires 82, for example power and signal cabling for the displays 220. As best illustrated in the cross section diagram of FIG. 8A, the joints 80 are capable of distributing the wires in multiple directions, including through the top and bottom of the joint and forward to the next segment of the articulated arm 200. FIG. 8B shows two wires 82a and 82b protruding out from the top and bottom directions of the joint 80, allowing equipment to be attached to both the top and bottom of the arms 200. For example, appendage arms and/or displays 220 can be suspended off the bottom of an arm 200, while task lighting or other equipment can be attached to the top of the arm 200. For more details of the segments and the joints 80 of the arm 200, see the above-identified application U.S. Ser. No. 11/093,075.

Figure 9A:
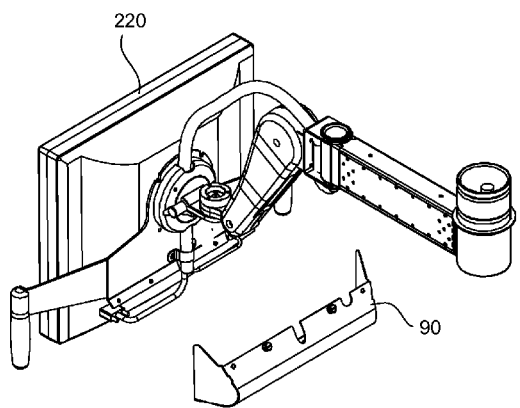
FIGS. 9A-9B illustrate a cowling plate used for covering the power and signal wires plugged into the back of the displays of the medical boom in accordance with the present invention.
Figure 9B:
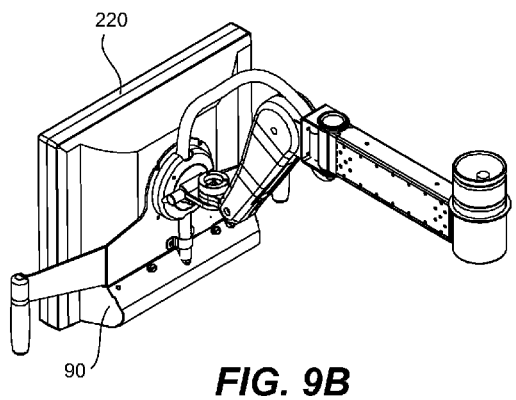

FIGS. 9A and 9B illustrate a cowling plate 90 used for covering the power and signal wires plugged into the back of the displays 220. In FIG. 9A, the cowling 90 is illustrated removed from the back of the display 220. In FIG. 9B, the cowling 90 is attached to the back of the display 220, covering the wires. In various embodiments, the cowling 90 can be made from a metal, plastic or any other hard or soft material. The cowling 90 is desirable for several reasons. It is easier to clean and keep sterile. It also protects the wires from contaminants and prevents the wires from being inadvertently pulled or removed from the displays 220, and is more aesthetically pleasing to look at.

Figure 10:
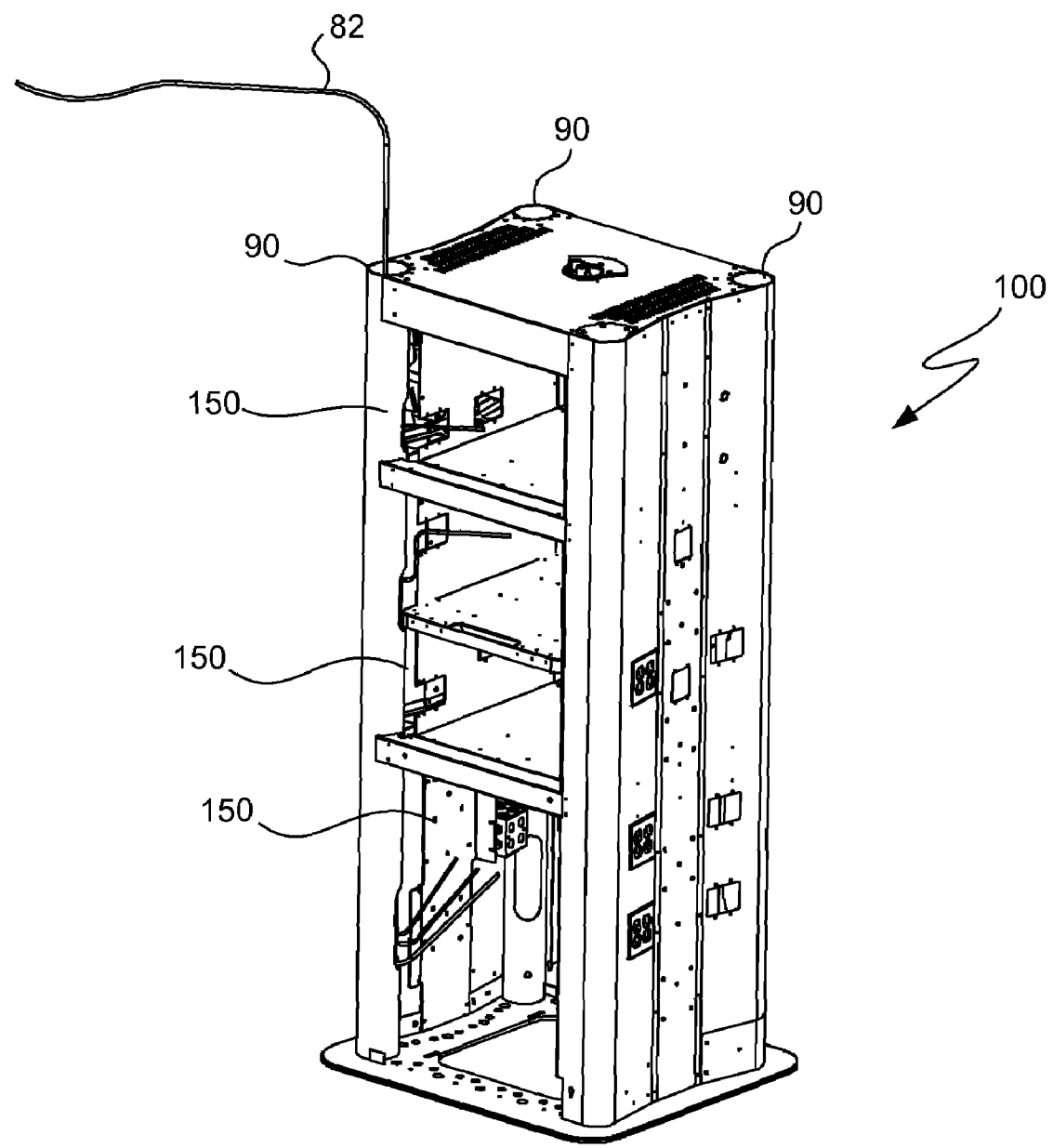
FIG. 10 illustrates the symmetrical features of the base cabinet of the medical boom according to the present invention.

Referring to FIG. 10, the symmetrical nature of the base cabinet 100 is shown. The cabinet 100 is symmetrical for a number of reasons. The articulated arms 200 (not illustrated) can be attached to any one of the four recesses 94 located in the four corners of the top of the cabinet 100. For the sake of illustration, a wire 82 is shown passing through one of the recesses 90. If an articulated arm 200 were attached, the wire would be routed through the arm 200 and joints 18 as described above. Within the base cabinet 100, the wire 82 would be connected to electrical equipment, power transformers, a power supply, etc. The equipment racks 300, 600 can also be inserted into the equipment bays 150 from either the side of the cabinet 100, either as shown in the diagram or in the opposing side of the diagram. In this regard, the medical boom 10 does not have a "front" or "back". On the contrary, the cabinet 100 is symmetrical, allowing the front panel or the equipment contained in the racks 300, 600 to be exposed through either side of the medical boom, depending on how it was installed. The symmetrical design of the medical boom 10 increases flexibility and allows the base cabinet 100 to be installed into virtually all operating room environments.

While this invention has been described in terms of several embodiments, there are alteration, permutations, and equivalents, which fall within the scope of this invention. For example, the stationary base does not necessarily have to be fastened to the floor of an operating room. It can also be attached to or affixed to the wall of an operating room. Further, while the present invention has been described as a medical boom for use in a hospital operating room, it does not necessarily have to be limited to this environment. Rather the boom of the present invention may be used in a dentist office, examination rooms, veterinary clinics, surgical suites, etc. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. A medical boom, comprising:

a stationary base configured to be installed in an operating room;

a plurality of boom arms, each of the plurality of boom arms being supported by the stationary base and configured to extend over an operating table in the operating room and having at least an associated pair of boom arm segments that are coupled together by a boom arm joint;

a plurality of appendage arms, each appendage arm being mounted on an associated boom arm and having at least an associated pair of appendage arm segments that are coupled together by an appendage arm joint, each of the appendage arms being configured to support an associated display monitor that can be positioned in the horizontal and the vertical planes substantially surrounding the operating table, wherein a first appendage arm of the plurality of appendage arms is mounted on an attachment joint mounted on one of the boom arm segments associated with a first one of the boom arms, the attachment joint being situated between first and second ends of the first one of the boom arms; and a bay in the stationary base configured to receive a removable equipment rack, the removable equipment rack including electrical equipment.

2. The medical boom of claim 1, wherein the bay further includes a plurality of slots in the stationary base and the removable equipment rack includes a plurality of trolley wheels designed to fit into the slots in the stationary base.

3. The medical boom of claim 1, wherein the bay in the stationary base includes a first opening to receive the equipment rack facing a first direction and a second opening to receive the equipment rack facing a second direction.

4. The medical boom of claim 1, wherein the bay further includes one or more guide rails and the equipment rack includes guides configured to engage the guide rails when inserting the equipment rack into the bay.

5. The medical boom of claim 1, further comprising a second bay, the second bay configured to include one or more of the following: shelves and/or drawers.

6. The medical boom of claim 1, wherein the bay includes a lock to lock the equipment rack in place in the bay.

7. The medical boom of claim 1, further comprising electrical wiring in the stationary base to electrically couple the electrical equipment in the rack when the rack is installed in the bay to a power source.

8. The medical boom of claim 1, wherein the boom arm further comprises a retractable handle to position the boom arm.

9. The medical boom of claim 8, wherein the boom arm comprises one or more segments coupled together by one or more joints respectively, and one or more appendage arms connected to the boom arm.

10. The medical boom of claim 9, wherein the one or more segments and joints are configured to route wires through the boom arm, wherein the wires can be selectively routed through either the top and/or the bottom of the boom arm so that equipment can be selectively mounted both above and/or below the boom arm.

11. The medical boom of claim 1, wherein the boom arm further comprises one or more articulated appendage arms to support one or more video displays over the operating table.

12. The medical boom of claim 11, further comprising one or more cowlings to cover wires coupled to the one or more video display respectively.

13. The medical boom of claim 1, wherein the stationary base is configured to support a plurality of the boom arms at one of the four corners of the stationary base.

14. The boom of claim 1, further comprising electrical wiring electrically coupled between one or more video displays supported by the boom arm to the electronic equipment in the rack when the rack is in the bay of the stationary base.

15. The boom of claim 14, wherein the electrical wiring provides video signals and power between the electronic equipment in the rack in the bay and the one or more video displays.

16. The medical boom of claim 1, wherein the stationary base is configured to support up to four of the boom arms and wherein the up to four boom arms each attach to a top corner of the stationary base respectively.

17. The medical boom of claim 1, wherein the attachment joint is the boom arm joint.

18. The medical boom of claim 1, wherein the first appendage arm and a second appendage arm of the plurality of appendage arms are mounted off a first boom arm of the plurality of boom arms and wherein a third appendage arm and a fourth appendage arm of the plurality of appendage arms are mounted off a second boom arm of the plurality of boom arms.

19. A medical boom, comprising:

a base having a bottom surface on its exterior, the bottom surface of the base arranged to be mounted on a floor of an operating room;

a first boom arm attached to and supported by the base, the first boom arm configured to extend over an operating table in the operating room and having at least at least three boom arm segments and at least two boom arm joints, ones of the at least three boom arm segments coupled to one another with ones of the at least two boom arm joints;

an appendage arm, the appendage arm being coupled with the first boom arm and supporting a first display monitor, wherein a height of the first display monitor can be adjusted without moving the first boom arm and without rotating the first display monitor, the height being the shortest distance between the first display monitor and the floor of the operating room when the bottom surface of the base is mounted on the floor of the operating room;

a second boom arm attached to and supported by the base, the second boom arm supporting a second display monitor;

a bay in the stationary base, the bay including a loading surface that is substantially parallel to the bottom surface of the base, the loading surface including one or more slots; and an equipment rack disposed within the bay and including a plurality of wheels, the plurality of wheels situated on a bottom end of the equipment rack and arranged for rolling the equipment rack across the floor of the operating room, the plurality of wheels of the equipment rack being situated within the one or more slots on the loading surface of the bay, wherein the equipment rack, the wheels and the loading surface of the bay are arranged such that the equipment rack is entirely disengaged from the bay by pulling on the equipment rack to roll the equipment rack out of the bay and onto the floor of the operating room.

* * * * *